(12) United States Patent
Schmitt

(10) Patent No.: US 9,549,668 B2
(45) Date of Patent: Jan. 24, 2017

(54) METHOD FOR DETERMINING AT LEAST ONE RELEVANT SINGLE IMAGE OF A DENTAL SUBJECT

(71) Applicant: Sirona Dental Systems GmbH, Bensheim (DE)

(72) Inventor: Bernhard Schmitt, Ludwigshafen (DE)

(73) Assignee: SIRONA DENTAL SYSTEMS GmbH, Bensheim (DE)

( * ) Notice: Subject to any disclaimer, the term of this patent is extended or adjusted under 35 U.S.C. 154(b) by 0 days.

(21) Appl. No.: 14/439,826

(22) PCT Filed: Oct. 30, 2013

(86) PCT No.: PCT/EP2013/072669
§ 371 (c)(1),
(2) Date: Apr. 30, 2015

(87) PCT Pub. No.: WO2014/067977
PCT Pub. Date: May 8, 2014

(65) Prior Publication Data
US 2015/0289756 A1    Oct. 15, 2015

(30) Foreign Application Priority Data
Oct. 30, 2012    (DE) .......................... 10 2012 219 865

(51) Int. Cl.
*G10L 15/26*    (2006.01)
*G10L 25/00*    (2013.01)
(Continued)

(52) U.S. Cl.
CPC .............. *A61B 1/24* (2013.01); *A61B 1/00009* (2013.01); *A61B 1/04* (2013.01); *A61C 9/004* (2013.01);
(Continued)

(58) Field of Classification Search
CPC .. G06F 19/322; G06F 17/3089; G06F 19/328; G06F 19/3418; G06F 19/3487
(Continued)

(56) References Cited

U.S. PATENT DOCUMENTS 6,964,567 B2    11/2005    Kerschbaumer et al.
7,856,248 B1 *  12/2010    Fujisaki ................ H04M 1/575
                                                   455/414.1
(Continued)

FOREIGN PATENT DOCUMENTS

DE         199 16 162 A1    10/2000
DE    10 2007 054 907 A1     5/2009
(Continued)

OTHER PUBLICATIONS

German Office Action mailed May 30, 2013 in German Patent Application No. 10 2012 219 865.2.
(Continued)

*Primary Examiner* — Charlotte M Baker
(74) *Attorney, Agent, or Firm* — Fitzpatrick, Cella, Harper & Scinto

(57) ABSTRACT

The invention relates to a method for determining at least one relevant single image, wherein a plurality of single optical images are generated during a continuous optical measurement (3) of a dental subject (1) to be recorded. During the optical measurement (3) an audio recording is generated by means of a microphone (4) and at least one speech sequence (12; 15; 28) spoken by a user (6) is recorded. The relevant single image (7; 8; 24) is then selected within a specified sequence duration between a start time (17, 18) and an end time of the speech sequence (12; 15; 28).

19 Claims, 3 Drawing Sheets

(51) Int. Cl.
| | |
|---|---|
| *A61B 1/24* | (2006.01) |
| *A61C 9/00* | (2006.01) |
| *G06F 19/00* | (2011.01) |
| *A61B 1/00* | (2006.01) |
| *A61B 1/04* | (2006.01) |
| *G10L 25/57* | (2013.01) |
| *H04N 5/91* | (2006.01) |
| *G10L 21/007* | (2013.01) |

(52) U.S. Cl.
CPC ............. *A61C 9/006* (2013.01); *A61C 9/0053* (2013.01); *G06F 19/321* (2013.01); *G10L 15/265* (2013.01); *G10L 25/57* (2013.01); *H04N 5/91* (2013.01); *G10L 21/007* (2013.01)

(58) Field of Classification Search
USPC ....... 704/235, 275; 705/3; 455/556.1, 414.1, 455/466, 555, 566; 348/66, E5.025; 434/263; 600/109, 112; 433/29
See application file for complete search history.

(56) References Cited

U.S. PATENT DOCUMENTS

| | | | | |
|---|---|---|---|---|
| 2003/0033151 | A1* | 2/2003 | Vozick | ................ A61B 5/7475 704/275 |
| 2006/0256193 | A1 | 11/2006 | Liu | |
| 2007/0026363 | A1 | 2/2007 | Lehmann et al. | |
| 2010/0284589 | A1 | 11/2010 | Thiel et al. | |
| 2014/0081667 | A1* | 3/2014 | Joao | ...................... G06F 19/322 705/3 |

FOREIGN PATENT DOCUMENTS

| | | |
|---|---|---|
| EP | 0 784 965 A2 | 7/1997 |
| EP | 1 252 859 A2 | 10/2002 |
| JP | 2005-97277 A | 4/2005 |

OTHER PUBLICATIONS

International Search Report in PCT/EP2013/072669 mailed Feb. 26, 2014.

International Preliminary Report on Patentability mailed May 5, 2015, in PCT/EP2013/072669.

Written Opinion of the International Search Authority in PCT/EP2013/072669.

* cited by examiner

METHOD FOR DETERMINING AT LEAST ONE RELEVANT SINGLE IMAGE OF A DENTAL SUBJECT

TECHNICAL AREA

The present invention relates to a method for determining at least one relevant single image, a plurality of optical single images being generated during a continuous optical measurement of a dental object that is to be recorded.

BACKGROUND OF THE INVENTION

From the existing art, methods are already known for archiving dental findings. In these methods, the dentist examines a patient and communicates the status and the finding to a dental assistant who enters the status or finding in a patient file, usually manually. This patient file can for example also be produced in special software.

DE 199 16 162 A1 discloses a dental laser system made up of a plurality of modules, the dental laser system having a read unit, a multimedia module, a scanner module, a protocol unit, and a speech control module. The speech control module can have a small microphone that for example can be integrated into a dental camera. Using the speech control module, comments can be added to the individually recorded images, which comments are subsequently archived and can be accessed later. The treating physician can also use the speech control module to input the treatment result, the treatment result being entered via a speech conversion program. The treatment results can subsequently be entered in record cards.

DE 10 2007 054 907 A1 discloses a method for the optical measurement of an object using a triangulation method by means of an optical recording device, a plurality of light sources and a plurality of diaphragm means being used in order to project a plurality of patterns onto the object simultaneously. For the measurement, advantageously a stripe projection method can be used, in which a pattern of parallel stripes is projected onto the object, and in this way a plurality of measurement points can be measured simultaneously.

In addition, archiving methods are known in which in additional video recordings of the relevant region in the oral cavity of the patient are recorded, and are manually assigned to the respective status or finding. Here, the video recording is usually actuated by actuating a switch on a dental camera, or a foot switch.

A disadvantage of this method is that if the dental assistant is inattentive, an incorrect assignment of the findings may occur. This can result in an error in treatment, or can require another examination of the patient.

Therefore, the object of the present invention is to provide a method that enables a reliable and time-saving assignment of single images, associated with a low outlay.

PRESENTATION OF THE INVENTION

The invention relates to a method for determining at least one relevant single image, a plurality of optical single images being produced during a continuous optical measurement of a dental object that is to be recorded.

During the optical measurement, a microphone is used to produce an audio recording, and at least one speech sequence spoken by a user is recorded. Subsequently, the relevant single image is selected within a specified sequence duration between a start time and an end time of the speech sequence. Within the determined speech sequence, that relevant single image is selected that was recorded at a time of least movement of the dental camera relative to the object to be recorded.

In this way, the relevant single image is selected having the lowest camera blur relative to the object. Such a single image has the fewest movement artifacts, and therefore has the best recording quality of all the single images of the respective speech sequence.

The optical measurement can for example take place using a video recording in which a plurality of single video images are recorded, or using an optical stripe projection method. In the stripe projection method, a stripe pattern is projected onto the object to be measured, and the three-dimensional surface of the object is determined based on the optical distortion of the stripe pattern. In this way, the overall object is continuously recorded in a plurality of 3-D images. The dental object can for example be the overall dental situation of the patient, or a part thereof, such as an upper jaw, a lower jaw, a preparation, or also individual teeth. The microphone for the audio recording can for example be integrated directly into the dental camera. Alternatively, the microphone can also be integrated into a headset that the user wears during the optical measurement, or can be integrated into a dental treatment unit. The user, such as a treating dentist or a dental assistant, articulates status information and/or finding information concerning the region of the object being examined during the optical measurement of the dental object. These speech sequences are then recorded and evaluated. The speech sequence can be recorded using a conventional video camera or using a microphone. Within the sequence duration of the speech sequence, the relevant single image is then selected and assigned to the respective speech sequence. The selection of the relevant single image can take place on the basis of various criteria, such as a low degree of local blurring.

An advantage of this method is that the relevant single image is automatically assigned to the respective speech sequence. In this way, mix-ups that could result in treatment errors are prevented.

A further advantage of this method is that the user, such as a treating dentist, can carry out the diagnosis independently without the assistance of a dental assistant. This shortens the duration of the diagnosis and is less susceptible to error.

Advantageously, in the processing of the audio recording, background noises can be filtered out by a filtering unit in order to improve the audio quality of the speech sequence.

As a filtering unit, for example a so-called noise gate can be used that amplifies speech signals and filters out background noise. This changes the dynamic range of the audio system, which is limited by the base noise of the audio system and by the maximum level without audible distortion. In this way, the audio quality of the recorded speech sequences is improved in order to determine the precise sequence duration.

In addition, the recorded speech sequences are converted from speech to text using speech recognition software. Here, the use of the filtering unit is also helpful.

Thus, the filtering unit is not activated until after the end time of the speech sequence, and is activated for a defined time duration, also referred to as the release time.

Alternatively, the filtering unit can also remain activated for the entire sequence duration.

In a further alternative, the filtering unit can remain activated during the entire optical measurement.

Advantageously, a maximum sequence duration and/or a minimum sequence duration of the speech sequence can be defined before the method is carried out.

In this way, the relevant single image is selected within the previously defined maximum sequence duration after the start time of the speech sequence, even if the user speaks for a longer time. In this way, a single image of a region of a dental situation is selected that corresponds to the respective speech sequence and to the finding information contained therein. The defined maximum sequence duration can for example be two seconds.

Advantageously, the sequence duration of the speech sequence can correspond to the duration of a contiguous flow of speech, where brief interruptions in the flow of speech are ignored that are shorter than a defined interruption duration.

In this way, the contiguous flow of speech is recognized as a single speech sequence despite brief interruptions. Hence when there are brief interruptions, new speech sequences are not started so that for the contiguous flow of speech, with interruptions, only one individual single image is selected in each case and assigned to this speech sequence.

Advantageously, the interruption duration can be a maximum of two seconds.

In this way, brief interruptions of the flow of speech of up to two seconds do not cause a termination of the speech sequence.

Advantageously, only one relevant single image can be selected within a speech sequence.

In this way, only one individual relevant single image is assigned to each speech sequence so that it is clear to the treating dentist which finding information and/or status information is associated with which region of the recorded dental situation.

Advantageously, the at least one speech sequence can contain status information and/or finding information, the status information and/or the finding information being converted from speech to text using speech recognition software.

In this way, the status information and/or finding information contained in the speech sequence is converted from speech into text and can be displayed in text form together with the relevant single images. In this way, the treating dentist is given a comprehensive overview of the overall situation of the dental object.

The speech sequence can in addition contain an anatomical position indication, such as "tooth 11 lingual," which can be converted from speech to text using the speech recognition software. This anatomical position indication is then assigned to the respective speech sequence together with the status and/or finding information. The treating physician can in this way diagnose the individual teeth sequentially, and can dictate the anatomical position indication with the respective finding information, such as "tooth 18 labial," "carious," "tooth 17 distal," "filling necessary." In this way, errors in the diagnosis due to the wrong assignment of the finding information are prevented.

Advantageously, the recognized status information and/or the finding information can be assigned in text form to the relevant single image of the respective speech sequence.

In this way, it is immediately evident to the treating dentist which status information and/or which finding information is associated with which single image.

Finding information can for example be a tooth affected with caries, a missing tooth, a replaced tooth, an implant having an intact crown, an implant that is to be removed, a clinically intact crown, a tooth that can be retained having partial substance defects, a root post cap that needs renovation, inadequate retention, a tooth that cannot be retained, a gap closure, a necessary crown, a bridge element that is to be inserted, a partial crown that is to be inserted, or a veneer that is to be inserted.

Advantageously, during the optical measurement of the overall object, a plurality of relevant single images can be selected for the respective speech sequences, the individual relevant single images being displayed using a display device.

In this way, the single images for the respective speech sequences can be displayed simultaneously using the display device such as a monitor. In this way, the treating dentist is given a quick overview of the overall situation of the dental object recorded, such as of an upper jaw or a lower jaw.

Advantageously, the speech sequences can include anatomical position information that is converted from speech to text by speech recognition software, the positions of the relevant single images relative to the recorded object being determined using the anatomical position information. Subsequently, using the display device, the relevant single images can be displayed at the determined positions relative to a virtual model of the object.

The user, such as a treating physician, thus dictates during the diagnosis the anatomical position information with the respective finding information, for example as follows: "tooth 18 labial," "carious," "tooth 17 distal," "filling necessary." The anatomical position indications "tooth 18 labial," "tooth 17 distal" are then recognized by the speech recognition software. Subsequently, the finding information "carious," "filling necessary" is assigned to the respective positions and is displayed in the virtual model of the object.

Alternatively, the positions of the relevant single images relative to the object recorded are determined using a pattern recognition method.

In this way, the single images are displayed in relation to the virtual model of the recorded object in order to facilitate the orientation. The user can also rotate the virtual model and can view it from different directions in order to better assess the finding information.

Advantageously, the selected relevant single images are sorted into a plurality of categories of status information and/or finding information.

In this way, the finding information, sorted according to a plurality of categories, can be displayed in order to give the treating dentist a simpler overview of the finding information, and thus to enable easier treatment planning. The finding information can for example be sorted into categories such as affected dental tissue, dental prosthesis parts to be removed, and dental prosthesis parts to be installed.

Advantageously, the optical measurement of the object can take place by video recording, and individual video images of this video recording can be the selected single images so that a relevant video image is selected for each speech sequence.

In this way, the optical measurement takes place via video recording using a conventional video camera integrated into a conventional dental handpiece.

Advantageously, the optical measurement of the object can take place using an optical three-dimensional stripe projection method, where a plurality of individual 3-D images of the object are produced and are combined to form a three-dimensional overall image. These individual 3-D images thus represent the single images that are to be selected so that a relevant 3-D image of the object is selected for each speech sequence.

In this way, the optical measurement of the dental object takes place using a dental camera based on the stripe projection method. This measurement enables the production of a three-dimensional overall image of the dental object.

BRIEF DESCRIPTION OF THE DRAWINGS

The present invention will be explained on the basis of the drawings.

EXEMPLARY EMBODIMENT

Figure 1:
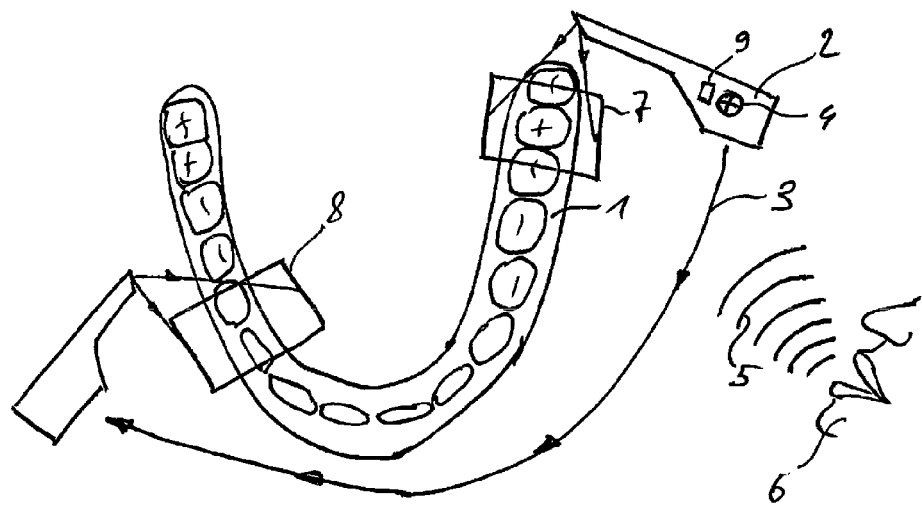
FIG. 1 shows a sketch illustrating the method.

FIG. 1 shows a sketch illustrating the method for determining relevant single images. A dental object 1, such as a lower jaw, is completely measured by an optical dental camera 2, the handheld camera 2 being moved around dental object 1 along a direction of movement 3 indicated by the arrows. During the optical measurement, single images are continuously recorded of different segments of the object 1. During the optical measurement, a microphone 4 integrated in the camera 2 is used to record an audio recording. At least one speech sequence 5 is recorded that is spoken by a user 6, such as a treating dentist or a dental assistant. Within a sequence duration of the first speech sequence 5, a first relevant single image 7 is then selected, and later, during the sequence duration of a second speech sequence, a second relevant single image 8 is selected. The selection of relevant single images 7 and 8 can take place on the basis of various criteria, such as the lowest amount of blur. Here, the movement of the camera 2 in relation to the dental object 1 is determined, and a relevant single image is selected at a local minimum of this relative movement. Such a single image thus has the fewest movement artifacts. For better processing of the audio recording, a filtering unit 9 is integrated in the camera 2 and amplifies the speech signals of the speech sequence 5 and filters out the background noise.

Figure 2:
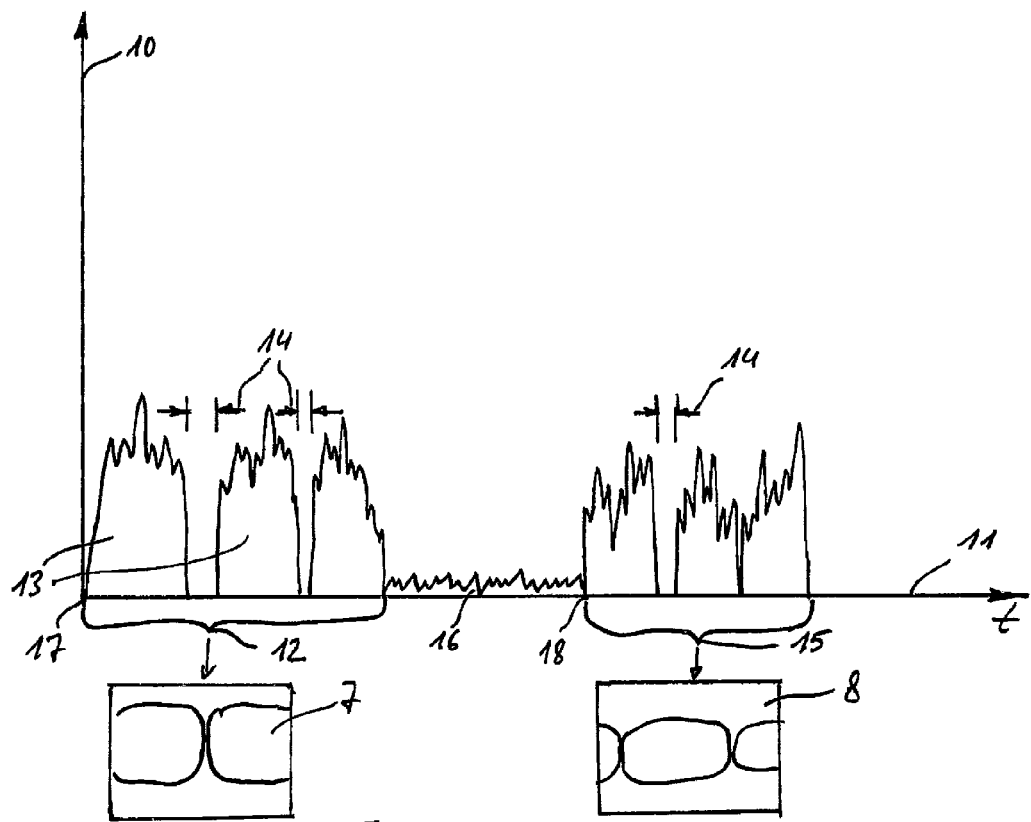
FIG. 2 shows a diagram illustrating the temporal sequence of the method.

FIG. 2 shows a diagram illustrating the sequence of the method. The magnitude of an amplitude 10 of the recorded audio signal is plotted on the time axis 11. Here, a first speech sequence 12 is made up of a plurality of parts 13 that form a contiguous flow of speech with brief interruptions 14. These interruptions 14 are however shorter than a defined interruption duration of, for example, two seconds, and are ignored. Thus, a new speech sequence is not begun until the interruption exceeds the defined interruption duration. Within the sequence duration of the first speech sequence 12, the first relevant single image 7 is selected and is assigned to this first speech sequence. Later, a second speech sequence 15 is recorded that also has a plurality of parts having a brief interruption 14. Within the sequence duration of the second speech sequence 15, the second relevant single image 8 is then selected and is assigned to this second speech sequence 15. Between the first speech sequence 12 and second speech sequence 15, the microphone 4 records the background noise 16 which, however, is filtered out by the filtering unit 9.

Alternatively, the relevant single image can also be selected within a defined time duration of, for example, two seconds after a first starting point 17 of the first speech sequence 12, and after a second starting point 18 of the second speech sequence 15, in order to detect single images from longer speech sequences.

The first speech sequence 12 and second speech sequence 15 can contain status information and/or finding information that can be converted from speech to text by speech recognition software. The detected text can contain anatomical position information that can be extracted and used for display purposes.

Figure 3:
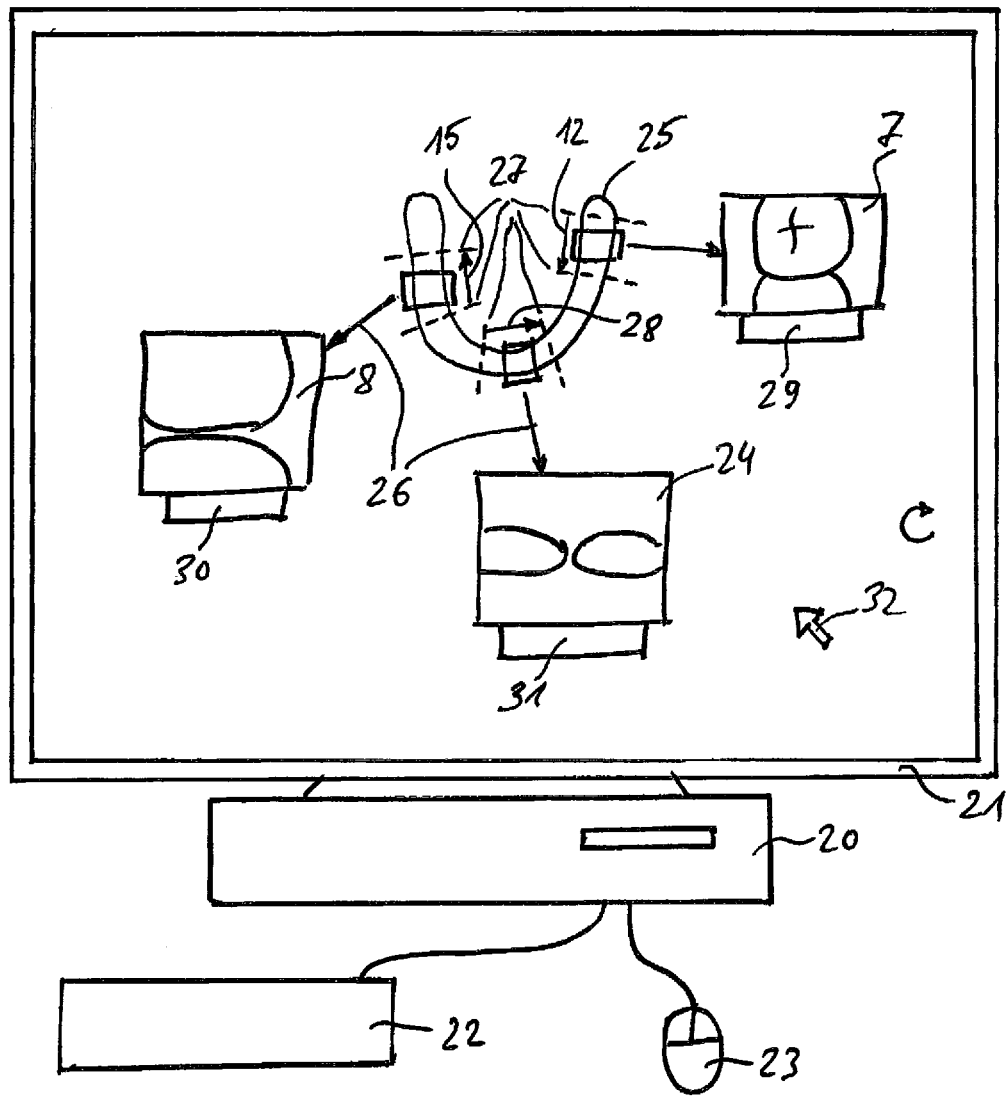
FIG. 3 shows a computer having a display device for representing the selected single images.
Figure 4:
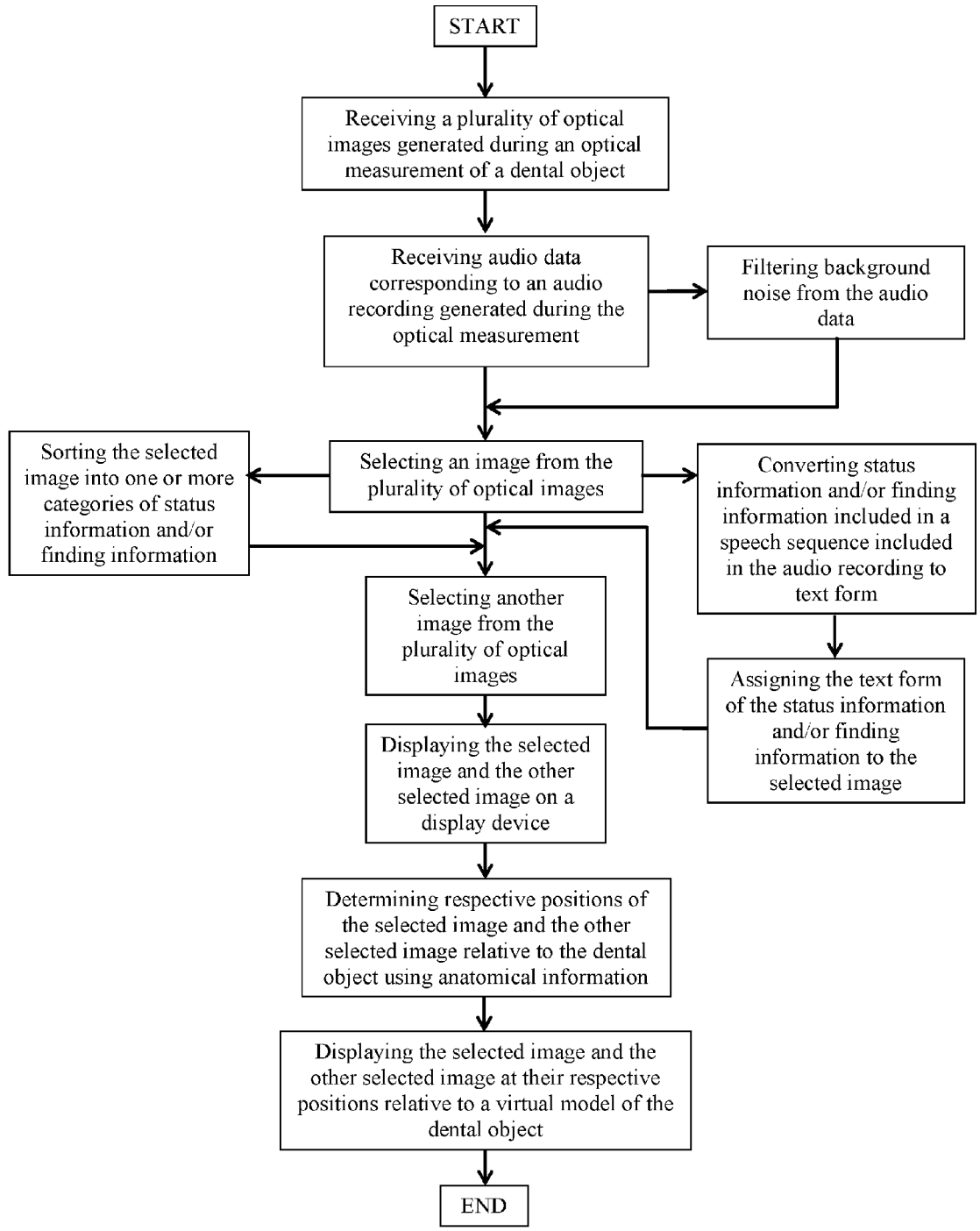
FIG. 4 shows a flow chart illustrating the method.

FIG. 3 shows a computer 20 having a display device 21 such as a monitor, and having input devices such as a keyboard 22 and a mouse 23. The first single image 7, second single image 8, and third single image 24 are displayed by the display device 21, in an enlarged exploded view, in a virtual model 25 of the object 1 to be recorded. Arrows 26 show the precise position of the selected single images 7, 8, and 24 relative to the model 25 of the object 1. Broken lines 27 indicate the start times and end times of the first speech sequence 12, second speech sequence 15, and a third speech sequence 28, and the direction of movement during the recording of speech sequences 12, 15, and 28 is shown by the arrows. In addition, a first item of finding information is displayed in text form in a box underneath first single image 7, a second item of finding information 30 is displayed underneath the second single image 8, and a third item of finding information is displayed underneath the third single image 24. In this way, the user, such as a treating dentist, is given a quick overview of the dental situation and the archived findings. Using the input devices 22 and 23, the user can change the direction of view of the model 25 by rotating the model via a cursor 32.

The selection of the detected single images per speech sequence can later be modified on the basis of a video sequence in order to achieve optimal results. Here, the positions of the single images, determined on the basis of the acoustic position information, can be checked for example using a pattern recognition method applied to the video sequence.

LIST OF REFERENCE CHARACTERS 1 dental object
2 dental camera
3 direction of movement
4 microphone
5 speech sequence
6 user
7 first relevant single image
8 second relevant single image
9 filtering unit
10 amplitude
11 time axis
12 first speech sequence
13 multiple parts of a speech sequence
14 brief interruption
15 second speech sequence
16 background noise
17 start time of the first speech sequence
18 start time of the second speech sequence
20 computer
21 display device
22 keyboard
23 mouse
24 third relevant single image
25 model of the object
26 precise position of the single images
27 start and end times of the speech sequences 28 third speech sequence
29 first finding information
30 second finding information
31 third finding information
32 cursor

The invention claimed is:

1. A method of selecting an image from a plurality of images, comprising:
receiving a plurality of optical images generated during an optical measurement of a dental object by a dental camera;
receiving audio data corresponding to an audio recording generated during the optical measurement;
selecting, based on the audio data and the plurality of optical images, an image from the plurality of optical images,
wherein the selected image was recorded between a start time and an end time of a speech sequence included in the audio recording and was recorded at a time during the speech sequence when a movement of the dental camera relative to the dental object was a local minimum.

2. The method as recited in claim 1, further comprising:
filtering background noise from the audio data to improve the audio quality of the speech sequence.

3. The method as recited in claim 2, wherein the filtering continues within a previously defined variable time.

4. The method as recited in claim 1, wherein a maximum duration of the speech sequence is predefined.

5. The method as recited in claim 1, wherein the speech sequence corresponds to the duration of a contiguous flow of speech, and wherein brief interruptions of the flow of speech that are shorter than a predefined interruption duration are ignored.

6. The method as recited in claim 5, wherein the predefined interruption duration is no more than two seconds.

7. The method as recited in claim 1, wherein the optical measurement of the dental object is by an optical three-dimensional stripe projection method, and
wherein the plurality of optical images of the dental object are combined into a three-dimensional overall recording.

8. The method as recited in claim 1, further comprising:
converting status information and/or finding information included in the speech sequence to text form.

9. The method as recited in claim 8, further comprising:
assigning the text form of the status information and/or finding information to the selected image.

10. The method as recited in claim 1, further comprising:
selecting, based on the audio data and the plurality of optical images, another image from the plurality of optical images,
wherein the other selected image was recorded between another start time and another end time of another speech sequence included in the audio recording and was recorded at a time during the other speech sequence when a movement of the dental camera relative to the dental object was a local minimum; and
displaying the selected image and the other selected image on a display device.

11. The method as recited in claim 10, further comprising:
determining respective positions of the selected image and the other selected image relative to the dental object using anatomical information included in the speech sequence and anatomical information included in the other speech sequence; and
displaying the selected image and the other selected image at their respective positions relative to a virtual model of the dental object.

12. The method as recited in claim 1, further comprising:
sorting the selected image into one or more categories of status information and/or finding information.

13. The method as recited in claim 1, wherein the plurality of optical images respectively correspond to individual frames of a video recording.

14. An apparatus for selecting an image from a plurality of images, comprising:
a computer configured to:
receive a plurality of optical images generated during an optical measurement of a dental object by a dental camera,
receive audio data corresponding to an audio recording generated during the optical measurement, and
select, based on the audio data and the plurality of optical images, an image from the plurality of optical images,
wherein the selected image was recorded between a start time and an end time of a speech sequence included in the audio recording and was recorded at a time during the speech sequence when a movement of the dental camera relative to the dental object was a local minimum.

15. The apparatus as recited in claim 14, wherein the computer is further configured to combine the plurality of optical images of the dental object into a three-dimensional overall recording.

16. The apparatus as recited in claim 14, wherein the computer is further configured to convert status information and/or finding information included in the speech sequence to text form.

17. The apparatus as recited in claim 16, wherein the computer is further configured to assign the text form of the status information and/or finding information to the selected image.

18. The apparatus as recited in claim 14, further comprising:
a display device,
wherein the computer is further configured to:
select, based on the audio data and the plurality of optical images, another image from the plurality of optical images, wherein the other selected image was recorded between another start time and another end time of another speech sequence included in the audio recording and was recorded at a time during the other speech sequence when a movement of the dental camera relative to the dental object was a local minimum, and
cause the display device to display the selected image and the other selected image.

19. The apparatus as recited in claim 18, wherein the computer is further configured to:
determine respective positions of the selected image and the other selected image relative to the dental object using anatomical information included in the speech sequence and anatomical information included in the other speech sequence, and
cause the display unit to display the selected image and the other selected image at their respective positions relative to a virtual model of the dental object.

* * * * *